United States Patent [19]

Vanden Hoek et al.

[11] Patent Number: 5,735,792
[45] Date of Patent: *Apr. 7, 1998

[54] SURGICAL INSTRUMENT INCLUDING VIEWING OPTICS AND AN ATRAUMATIC PROBE

[75] Inventors: John C. Vanden Hoek, Elk River; Mark Francis Brown, Coon Rapids; Victor Roy Blackledge, Cologne; Miles A. Finn, Minneapolis; Richard L. Shockey, Coon Rapids; Thomas C. Barthel, Becker, all of Minn.

[73] Assignee: Clarus Medical Systems, Inc., Minneapolis, Minn.

[ * ] Notice: The term of this patent shall not extend beyond the expiration date of Pat. No. 5,512,034.

[21] Appl. No.: 638,680

[22] Filed: Apr. 29, 1996

Related U.S. Application Data

[63] Continuation-in-part of Ser. No. 233,013, Apr. 25, 1994, Pat. No. 5,512,034, which is a continuation-in-part of Ser. No. 981,641, Nov. 25, 1992, abandoned.

[51] Int. Cl.⁶ .................................................. A61B 1/00
[52] U.S. Cl. .......................... 600/138; 606/13; 607/88
[58] Field of Search ........................... 600/104, 109, 600/114, 115, 116, 117, 129, 138, 245, 204, 210; 606/7, 13, 14, 15, 16, 17, 160, 161; 607/88, 89

[56] References Cited

U.S. PATENT DOCUMENTS

| | | | |
|---|---|---|---|
| 2,076,741 | 4/1937 | Peck | 600/129 X |
| 3,799,150 | 3/1974 | Bonnet | 600/129 X |
| 4,793,326 | 12/1988 | Shishido | 600/114 X |
| 4,802,461 | 2/1989 | Cho | 128/7 |
| 4,867,138 | 9/1989 | Kubota et al. | 128/6 |
| 5,156,604 | 10/1992 | Hessel et al. | 606/15 |
| 5,158,086 | 10/1992 | Brown et al. | 128/662.03 |
| 5,230,621 | 7/1993 | Jacoby | 433/29 |
| 5,263,928 | 11/1993 | Trauthen et al. | 600/129 X |
| 5,337,735 | 8/1994 | Salerno | 128/11 |
| 5,505,686 | 4/1996 | Willis et al. | 600/114 X |
| 5,512,034 | 4/1996 | Finn et al. | 600/138 |

*Primary Examiner*—Beverly M. Flanagan
*Attorney, Agent, or Firm*—Olson & Hierl, Ltd.

[57] ABSTRACT

A surgical instrument incorporating visualizing optics is disclosed. The instrument comprises a handle supporting a rigid hollow shaft, an expanded tip is located on the distal end of the shaft providing a surface that will not tear or easily penetrate tissue. A fiber-optic assembly, containing at least one illumination transmitting fiber, a plurality of image-carrying fibers and an objective lens mounted near the distal end of the image fibers runs the length of the shaft. The objective lens is positioned relative to an opening in the tip allowing viewing. Light for illuminating the surgical site passes through one or more illumination fibers and through the opening in the tip of the probe. Light reflected from the tissue at the tip of the probe is focused onto the distal face of the image bundle by an objective lens and is then transmitted to the proximal end of the image bundle. Connectors on the proximal ends of the illumination fibers and image fibers facilitate their being coupled to an illumination source and a viewing device.

35 Claims, 5 Drawing Sheets

SURGICAL INSTRUMENT INCLUDING VIEWING OPTICS AND AN ATRAUMATIC PROBE

RELATED APPLICATION

This application is a continuation-in-part of earlier filed application Ser. No. 08/233,013 filed Apr. 25, 1994, now U.S. Pat. No. 5,512,034 which is a continuation-in-part of application Ser. No. 07/981,641 filed Nov. 25, 1992 now abandoned.

FIELD OF THE INVENTION

This invention relates generally to surgical instruments, and more particularly to an instrument incorporating a probe for observing body structures hidden from direct view, the instrument also incorporating viewing optics whereby the structures can also be indirectly viewed.

DISCUSSION OF THE PRIOR ART

During many surgical procedures, the surgeon is often required to reach into corners and around obstructions to feel or view tissue structures. Many of the obstructions must be carefully moved, or elevated, to examine those structures concealed from view.

Additionally, during a procedure such as a laminectomy/ discectomy, the surgeon is often required to determine whether a disc in the spine has become herniated to the point where it bulges out and compresses a nerve resulting in back pain. The surgeon opens up the back and excises part of the disc. Because the spinal canal protects the spinal cord, many important structures are hidden from direct access and view.

The surgeon then typically uses an L-shaped probe having an atraumatic tip, preferably bulbous, to reach under the dura mater to determine by sense of touch if the bulge in the disc has been sufficiently reduced by excision of the disc material so that pressure on the nerve will no longer occur. However, this can only be done by tactile feel because direct vision is not possible. Such a probe may also be used to allow tactile location of the foramen to determine if the spinal nerves are passing freely through the opening.

A probe of the type described is more clearly illustrated in *Microsurgery of the Spinal Cord and Surrounding Structures* by Wolfgang Seeger, Springer-Verlag, New York, 1982, pg. 363. Figure G on that page depicts a view through an operating microscope where a right-angled probe having a bulbous tip is reaching under the dura mater in the course of a laminectomy/discectomy procedure. While a skilled surgeon is able to deduce the state or condition of the disc structure by relying only on the tactile response provided by the L-shaped ball probe, the addition of a means for visualizing the tissue structures encountered by the probe tip would significantly enhance the safety and efficacy of the surgical procedure.

For such a probe to work, it must be small and light to provide the proper tactile feel. However, viewing around corners is not possible. Endoscope systems provide for viewing, but by their nature, are usually large and bulky. In addition, the distal end of a viewing system is generally ill suited to use for tactile sensing. Due to the bulky nature of such systems, the ends are not the right shape for direct contact and pressure on tissue and damage to tissue will usually result.

Other invasive probe systems are disclosed in Kubota et al. U.S. Pat. No. 4,867,138 entitled "Rigid Electronic Endoscope"; Hessel et al. U.S. Pat. No. 5,156,604 entitle "Small Probing Hook For Arthroscopy"; Brown et al. U.S. Pat. No. 5,158,086 entitled "Invasive Probe System"; Jacoby U.S. Pat. No. 5,230,621 entitled "Endoscopic Method And Device For Subgingival Dental Procedures"; and Heckele U.S. Pat. No. 4,593,682 entitled "Endoscope."

The probe disclosed in the Kubota et al. patent has an asymmetric tip with electronic imaging means. An opening is provided adjacent the tip and imaging means to provide a path for either an instrument or fluid to the exterior of the probe. Unfortunately, the device of the Kubota et al. patent does not possess effective tactile capabilities. Further, the image of the tissue provided by the Kubota et al. probe is obstructed by the instrument.

The probe disclosed in the Hessel et al. patent has a probing hook that has a slidable laser fiber guided at the distal end of the probing hook. The Hassel et al. patent discloses an arthroscopic instrument for diagnostic and therapeutic purposes, e.g. laser surgery, without an exchange of instruments. This device is not designed for endoscopic use. Because the probe of the Hessel et al. patent teaches the use of a displaceable laser fiber which extends beyond the probe, it is poorly suited for the combination of tactile feel and viewing.

The Brown et al patent discloses a probe system having a probe head that may provide imaging or combined imaging-treatment. The probe is resilient and articulated, which greatly limits its tactile capabilities. The addition of articulation results in a large shaft and bulky handle which makes good tactile feel by the surgeon difficult, if not impossible.

The Jacoby patent discloses a dental method and device for removing deposited material from subgingival tooth surfaces. An optical head is positioned adjacent a working part or blade of the instrument and aimed at an angle to permit illumination and endoscopic visualization of an area immediately in front of the leading edge of the working part or blade of the instrument. Because the view of the working area is obstructed by the working part, the device has limited endoscopic capabilities. The device also has limited tactile capabilities because the hook-shaped construction prevents effective response in all directions. In fact, the Jacoby device is not designed for tactile feel but to scrape deposits off teeth.

The probe disclosed in the Heckele patent has a rigid distal longitudinal member having a distal extremity which may be angled. A light duct and an image duct having an objective lens are also included. The Heckele patent probe is used simply to view the prefrontal sinuses and does not possess effective tactile capabilities.

What is needed is a small, easy to use instrument which allows a surgeon to observe tissue which is normally hidden from direct view. The present invention satisfies this desire.

SUMMARY OF THE INVENTION

The present invention provides an improved surgical instrument for use in the conduct of surgical procedures. The surgical instrument has an expanded atraumatic tip that includes endoscopic viewing capabilities so that the surgeon can observe tissue structures which would otherwise be hidden from direct view. The combination of viewing optics with a probe allows tissue structures not otherwise visible through an incision to be simultaneously accessed and observed.

The surgical instrument includes an elongated, rigid shaft having a proximal end, a distal end and a lumen extending between the ends. A handle is affixed to the proximal end of the shaft and an atraumatic expanded tip is formed on or otherwise attached to the distal end of the tubular shaft. The tip defines a surface opening that communicates with the lumen of the shaft. The opening may be coaxial with the lumen.

A fiber-optic assembly, including a plurality of optical image fibers as in a bundle and, preferably, one or more illumination fibers, extends through the lumen of the shaft. The distal end of the optical image fibers have a planar face. An objective lens, cooperating with the distal end of the image fibers, is mounted within the lumen to receive light rays entering the opening formed in the tip and create an image on the face of the image fibers.

The fiber-optic assembly also passes through a bore in the handle, and preferably on its proximal end are first and second connectors for coupling the illumination fibers in the fiber-optic assembly to an external light source and the image fibers to an appropriate display device, such as an eyepiece or a video camera and an associate CRT display terminal. Alternatively, the fiber-optic assembly may be connected to a camera, such as a CCD camera mounted on the handle.

The surgical instrument of the present invention can also be used with another surgical instrument during a surgical procedure. For instance, the surgical instrument of the present invention may be inserted into the body for palpating and viewing tissue. Because the tip of the present invention displaces tissue, a space may be created between the tissue such that another instrument, such as another surgical instrument according to the present invention, may also be inserted into the body and positioned relative to the other surgical instrument to palpate tissue.

BRIEF DESCRIPTION OF THE DRAWINGS

The foregoing features and advantages of the invention will become more apparent to those skilled in the art from the following detailed description of the preferred embodiment, especially when considered in conjunction with the accompanying drawings in which.

DESCRIPTION OF THE PREFERRED EMBODIMENT

Figure 1:
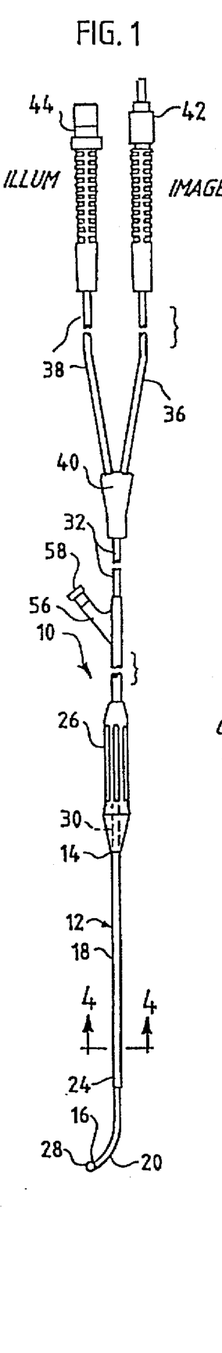
FIG. 1 is a side elevation view of a surgical instrument constructed in accordance with the present invention.

Referring to FIG. 1, there is illustrated a surgical instrument constructed in accordance with the present invention identified generally by numeral 10. The instrument 10 comprises an elongated rigid tubular shaft 12 having a proximal end 14 and a distal end 16. As can be seen from the greatly enlarged cross-sectional view of FIG. 4, the shaft 12 includes an outer tube 18 surrounding an inner tube 20 with the inner tube 20 defining a lumen 22 extending between the proximal end 14 and the distal end 16. The outer tube 18 terminates at 24 (FIG. 1), which is a predetermined distance proximal of the distal end 16 of the instrument 10.

Figure 4:
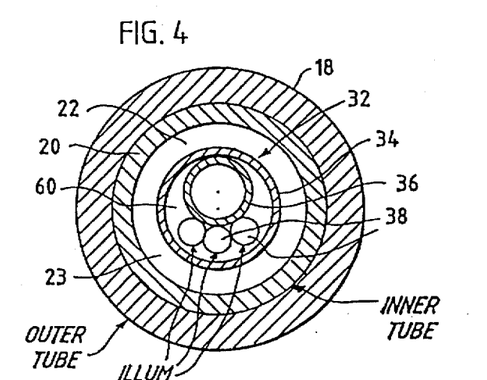
FIG. 4 is a cross-sectional view taken along the plane 4—4 in FIG. 1.

Outer tube 18 and inner tube 20 provide greater rigidity to the instrument in the zone proximal of the terminus 24 of the outer tube 18. The outer tube 18 may be formed from stainless steel. The rigidity provided by the coaxially disposed tubular shaft 12 further enhances the tactile response of the instrument 10. The inner tube 20 may be constructed of stainless steel or, if desired a material that is somewhat more malleable such that it is capable of being bent by the surgeon and still maintain the instrument's tactile response for use as a tactile probe.

Referring again to FIG. 1, it can be seen that the proximal end 14 of the shaft 12 is joined to a handle 26. It is preferred that shaft 12 is generally tapered from the proximal end 14 to the distal end 16, which provides greater rigidity and further enhances tactile response of the shaft 12 at its proximal end 14. In accordance with an embodiment of the invention, a segment of the inner tube 20, which is proximal of the terminus 24 of the outer tube 18, is arcuate with a bend having a desired angle in the range of from about 20 degrees up to 90 degrees, and a length in the range of from about 8 mm to 15 mm. Integrally formed on or otherwise affixed to the distal end 16 of the shaft 12 is a rigid, atraumatic bulbous tip 28. The tip 28 is preferably generally spherical in shape and of a size which would not tend to penetrate into the tissue being probed. The sphere or ball tip 28 may have a diameter of about 3 mm., but that size is only indicated for the purpose of illustration.

The desired diameter of the tip 28 varies according to its intended use. The tip 28 may have a different diameter depending on its use. For example, the diameter of tip 28 may be smaller than 3 mm for use in the cervical spine. The diameter of tip 28 is expanded to be greater than the diameter of the distal end 16 to enhance tactile feedback. The diameter of tip 28 may, however, be either greater or less than the diameter of the proximal end 14.

Figure 7:
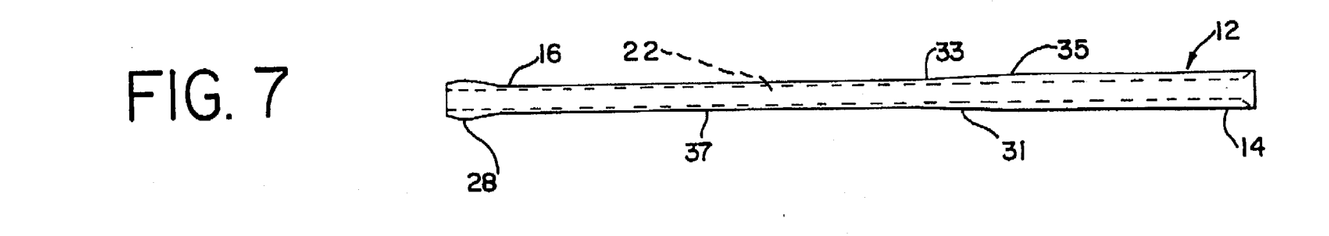
FIG. 7 is a greatly enlarged side elevation view of an alternative embodiment for the shaft and tip of the instrument of FIG. 1.

As can be seen from FIG. 7, the shaft 12 may consists of a single tube 37. The tube defines lumen 22 and extends from proximal end 14 to distal end 16, and may further form the bulbous tip 28. The tube 37 may consists of a metal or metal alloy such as stainless steel and, if desired, be malleable.

The tube 37 including bulbous tip 28 may be constructed by methods such as hollow center grinding or turning on a screw machine. Preferably, the tube 37 is tapered such that the outer diameter at the proximal end 14 is in the range of from about 2.5 mm to 2.4 mm, and the outer diameter at the distal end 16 is in the range of from about 1.9 mm to 1.8 mm.

As shown in FIG. 7, the tube can be tapered in a single area 31 with a generally uniform outer diameter from distal end 16 to 33 and from proximal end 14 to 35. The tube 37 preferably has a smaller outer diameter between 16 and 33 than the outer diameter between 35 and 14.

The bulbous tip 28 is expanded, meaning it has an outer diameter which is greater than the outer diameter at distal end 16. However, depending on the application of the surgical instrument, the outer diameter of the bulbous tip 28 may be either greater or less than the outer diameter at proximal end 14.

The tapering enhances the tactile response of the shaft 12 at its proximal end 14. Further, if the tube 37 is construed of malleable material, then both the outer diameter and the rigidity of the shaft 12 will decrease towards the distal end 16 of the tube 27. This allows for ease in shaping the shaft 12 about distal end 14 to position the tip 28 as desired.

Figures 5, 6:
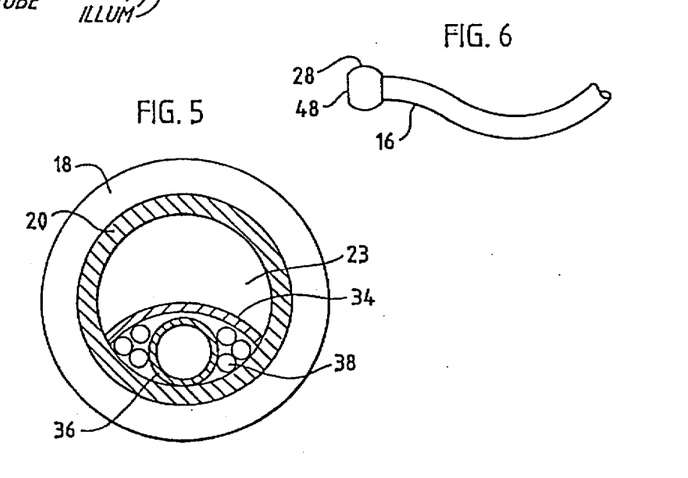
FIG. 5 is an alternative cross-sectional design similar to that of FIG. 4.
FIG. 6 is an alternative embodiment for the distal end of the instrument.

The present invention also contemplates other shapes for tip 28, such as the prolate or oblate tip shown in FIG. 6. Typically, prolate tips pass through tissue easily whereas oblate tips provide better tactile response. The tip is preferably rigid or incompressible in order to facilitate tactile response.

A bore 30 is formed longitudinally through the handle 26 and that bore is preferably in generally coaxial alignment with the lumen 22 of the inner tube 20. Passing through the bore 30 and the lumen 22 is a fiber-optic assembly 32.

In accordance with the embodiment of FIG. 4, the fiber-optic assembly 32 preferably includes an outer sheath 34 surrounding an assembly of image fibers 36 and preferably at least one, or more preferably several, illumination fibers 38. Preferably, an annular space 23 is formed in the lumen 22 between inner tube 20 and sheath 34 as illustrated in FIG. 4. This space can be used to introduce a flushing fluid as discussed below.

In the alternative embodiment of FIG. 5, however, the image fibers 36 and illumination fibers 38 are not axially disposed. Instead, image fibers 36 and illumination fibers 38 are located between inner tube 20 and sheath 34. This configuration defines a space 23 having less surface area and a greater cross-section area than space 23 in FIG. 4 to provide greater conduction of fluid with less pressure.

Typically, an irrigation fluid flow rate of about 25 cc/min. is required to clear blood away from lens 50 during a surgical procedure. However, most pressure cuffs provide up to about 300 mm Hg pressure. Some lumen configurations may not be able to achieve that flow rate with this pressure. Space 23 of FIG. 5, however, can provide that rate with this pressure.

Referring back to FIG. 1, disposed proximal of the handle 26 is a molded plastic hub member 40 surrounding a junction where the illumination fibers 38 and the image fibers 36 bifurcate into separate branches. Affixed to the proximal end of the bundle of image fibers 36 is a connector 42 which is adapted to mate with a viewing device (not shown), such as an optical eyepiece or a video camera providing a desired degree of magnification. The illumination fibers 38 also terminate at their proximal end in a connector 44 which is adapted to connect to a light source (not shown).

Figure 2:
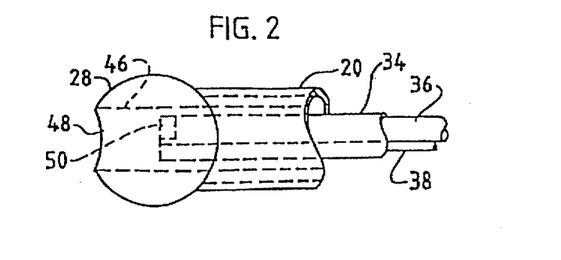
FIG. 2 is a greatly enlarged view of the atraumatic tip on the surgical instrument of FIG. 1.

In the embodiments of FIGS. 2 and 6, the atraumatic (ball) tip 28 defines an opening 48 leading to a hollow chamber 46 formed within the tip. Preferably, the chamber has a diameter large enough to receive distal end 16 of the shaft. The chamber 46 communicates with the generally circular surface opening 48 through the sphere's surface at its most distal end. Fiber-optic assembly 32 terminates within the hollow chamber 46 and an objective lens 50 is provided at the distal end of the image fibers 36 in assembly 32. By mounting the objective lens 50 a predetermined distance relative to the surface opening 48 in the distal end of the bulbous tip, the distal surface of the tip used for probing tissue can be brought into the focus range of the lens. Further, the tool itself does not obstruct the view of the tissue being probed and the lens 50 does not contact the tissue while in use. This allows for probing and viewing simultaneously without changing the configuration of the instrument.

As can be seen in FIG. 1, the arcuate bend in inner tube 20 may be less than 90 degrees. As the arcuate bend in the tube 20 approaches 90 degrees, however, stress between the interface of the lens 50 and image fibers 36 is increased. To overcome this, it is preferred in the present invention to increase the distance between the arcuate bend in tube 20 and tip 28. To further lessen this stress, another bend can be located proximal to distal end 16 as illustrated in FIG. 6.

When a source of light is coupled to the connector 44, it passes through the illumination fibers 38 and out through the opening 48 in the spherical tip 28. Objects illuminated by such light reflect an image back through the objective lens 50 and the image fibers within the image bundle 36 to the viewing device (not shown) coupled to the connector 42.

In use, the surgeon is able to insert the instrument through a surgically created opening in the body and then by manipulating the handle can position the instrument so as to feel tissue structures of interest. Because of the incorporation of the fiber-optic assembly 32 within the instrument, the tissue structures being approached and felt with the atraumatic tip 28 can also be visually observed.

Figure 3:
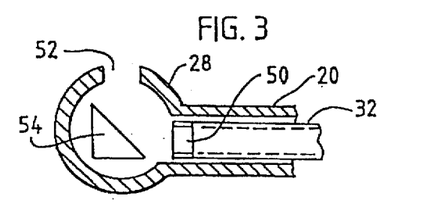
FIG. 3 is a greatly enlarged cross-sectional view of the atraumatic tip portion of the surgical instrument of FIG. 1 when constructed in accordance with an alternative embodiment.

While FIG. 2 depicts an end-viewing instrument, the cross-sectional view of FIG. 3 shows the manner in which the atraumatic tip can be modified to offer a side-viewing instrument. The bulbous or spherical tip 28 in FIG. 3 is generally hollow and has an opening 52 formed therein which is at an angle, approximately 90 degrees as illustrated, to the longitudinal axis of the shaft 20. Suitably disposed within the confines of the hollow spherical tip 28 is an optical means, such as a prism or mirror 54, which is positioned to refract or reflect light emanating from the ends of the illumination fibers 38 within the assembly 32 out through the opening 52. Prism 54 picks up the reflected image observed through the opening 52 and presents it on the objective lens 50. The prism preferably has a plurality of facets and a reflective surface on at least one of the facets.

Referring once more to FIG. 1, a Y-fitting 56 having a Luer lock 58 on its proximal end is joined to the handle 26 and contains a lumen that is in fluid communication with the lumen 22 in the shaft 12. This allows a source of irrigation or flushing liquid to be injected through the Luer fitting 58 and the Y-fitting 56 so that it will exit the lumen 22 of the fiber-optic assembly 32 in a fashion to insure that the objective lens 50 can be flushed clean of blood or other debris that might otherwise occlude the image being viewed.

Further, the irrigation fluid exiting the tip 28 of the surgical instrument 10 can be used to hydrodissect soft tumors or hematomas. In such a procedure, the surgeon increases the pressure provided by the irrigation fluid source such that fluid exiting the tip 28 of the instrument 10 will have sufficient force to displace unwanted structures. For example, using a fluid flow rate of about 50 milliliters per minute through the lumen 22 may provide suitable pressure to dissect soft tumors in a procedure involving inter-cranial work.

Using the annular space defined between tubes 18 and 20, and the outer sheath 34 minimizes the diameter of the shaft 12 and maximizes the possible flow rate of flushing liquid. This provides an annular flush that spreads fluid around the circumference of fiber-optic assembly 32 of the distal end 16 and out the space 23 to insure clearness in the entire field of view of fiber-optic assembly 32. This same annular space or channel or, alternatively, a separate lumen or channel can be used to aspirate fluids. As a further alternative, a separate channel or lumen as shown in FIG. 5 disposed parallel to fiber-optics assembly 32 can also be used for providing the flushing liquid. These separate lumen or channels are preferably located within shaft 12.

For example, the outside diameter of the shaft member or outer tube 18 may be approximately ⅛ in. and may be about 5 in. long. The shaft portion or outer tube 20 may be about 1 in. in length and 2 mm. in diameter.

The number of illumination fibers and their diameters are selected to provide adequate light intensity. Typically, there might be three plastic illumination fibers, each of a diameter of 250 microns. Alternatively, approximately 100 glass fibers of 50 micron diameter each might be used. The light emitted by the illumination fibers illuminates the tissue exterior to the tip 28 to be viewed. Light reflected from the tissue is collected by the objective lens 50 and focused on a preferred planar face defined by the distal ends of image fibers 36 of fiber-optic assembly 32. Typically, this assembly including image fibers 36 may include up to 10,000 individual glass fibers which provides excellent resolution of the image focused by the objective lens 50.

While the embodiment illustrated in the drawings shows only a single fiber-optic bundle traversing the length of the probe and cooperating with an opening formed in the bulbous atraumatic tip thereof, it is also contemplated that a second fiber-optic bundle may also be routed through the handle and shaft of the instrument and have its objective lens properly positioned relative to the opening to provide a binocular view along separate optical axes.

In the alternative embodiment of FIGS. 8–11, the surgical instrument 110 includes an optics harness assembly 181 removably mounted on a probe assembly 162. The instrument 110 also preferably includes a flush assembly 160 which can be removably mounted between the probe assembly 162 and the optics assembly 181. One or more of the optics harness assembly 181, probe assembly 162 and flush assembly 160 can be made disposable. For example, the probe assembly 162 and flush assembly 160 can be steam sterilized and reused while the more delicate optics harness assembly can be disposed and replaced after use.

Figure 8:
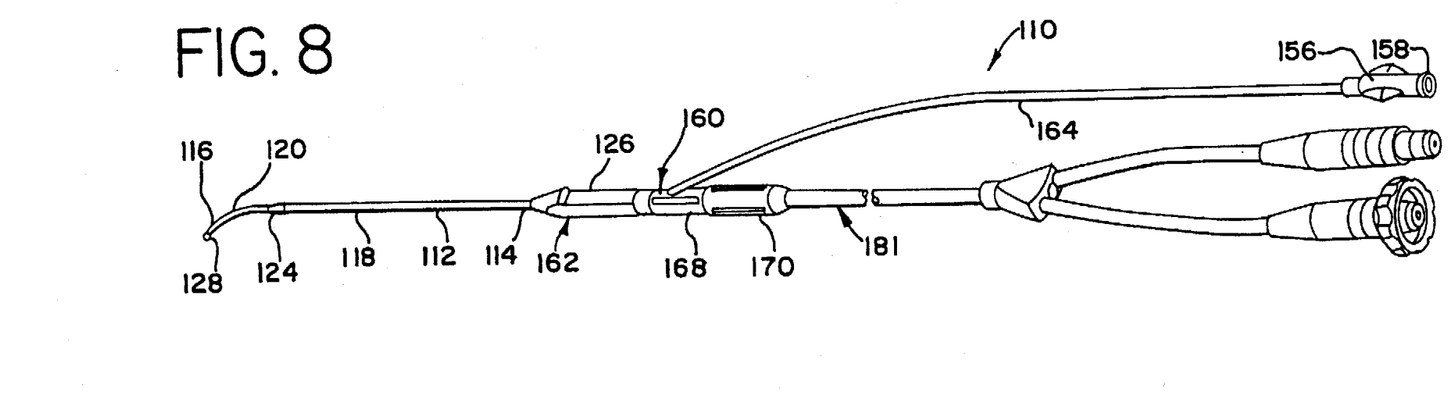
FIG. 8 is a side elevation view of yet another embodiment of a surgical instrument constructed in accordance with the present invention.
Figure 10:
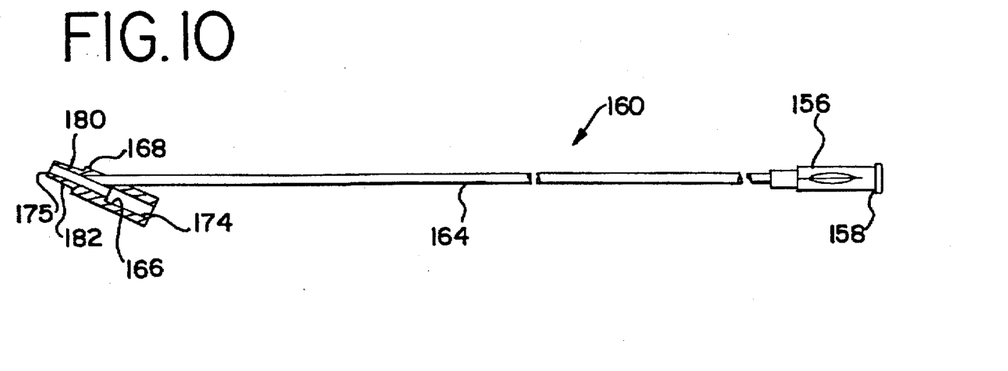
FIG. 10 is a partial cross-sectional view of the disposable flush assembly depicted in FIG. 8.

As can be seen from FIGS. 8 and 10, the flush assembly 160 includes a flexible hose 164 containing a lumen in fluid communication with the bore 166 of a Y-connector 168. Attached to the distal end of the hose 164 is fitting 156 having luer lock 158. The fitting 156 connects to a source of irrigation or flushing liquid which flows through the hose 164 and into the Y-connector bore 166.

Figure 9:
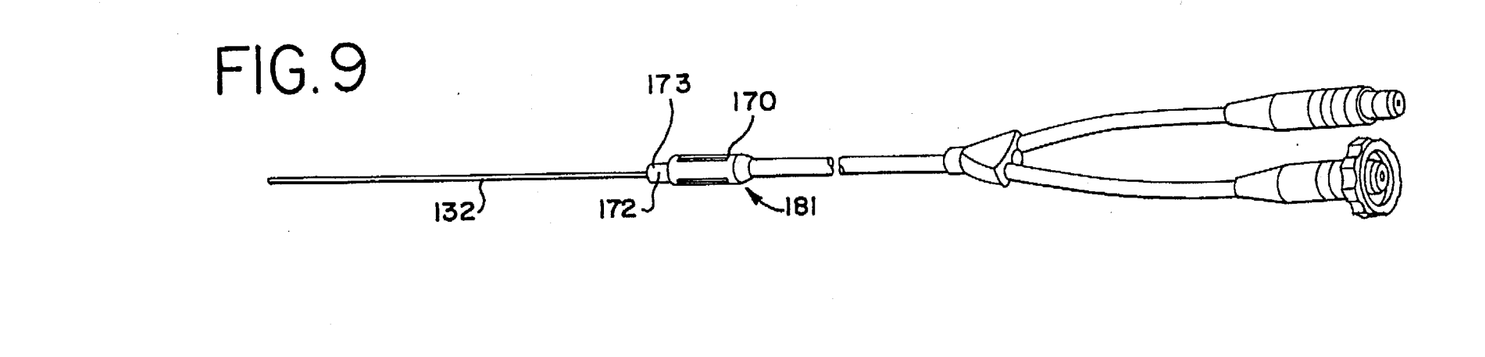
FIG. 9 is the surgical instrument of FIG. 8 with the disposable probe assembly and flush assembly removed.

The Y-connector 168 is detachably secured to endoscope connector 170. As illustrated by FIGS. 9 and 10, the fiber-optic assembly 132 which coaxially extends from connector 170 is inserted through the Y-connector bore 166. Likewise, tapered luer fitting 172 of connector 170 is extended into the Y-connector bore 166. Outer surface 173 of the luer fitting 172 frictionally adjoins against inner surface 174 of the Y-connector 168 to provide a tightly sealed interconnection. The seal ensures that liquid injected into the bore 166 from connector 156 will flow around the fiber-optic assembly 132 and exit only from distal open end 175 of T-connector 168.

Attached to the T-connector distal end 175 is the disposable probe assembly 162 that includes an elongated rigid shaft 112 of similar construction as that depicted in FIG. 1. The shaft 112 includes inner tube 120 surrounded by outer tub 118 and terminating at 124. The proximal end 114 of the shaft 112 is joined to handle 126. Further, atraumatic bulbous tip 128 is interconnected to the distal end 116 of the shaft 112.

Figure 11:
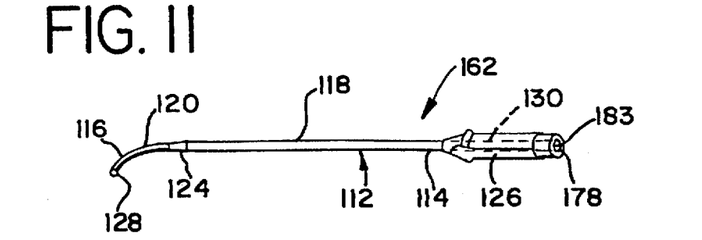
FIG. 11 is a side elevation view of the disposable probe assembly illustrated in FIG. 8.

As depicted by FIG. 11, bore 130 longitudinally extends through the handle 126 and is preferably in generally coaxial alignment with the lumen of the inner tube 120. The proximal end of the handle 126 includes an opening 178 in communication with the bore 130.

The handle 126 is detachably secured to the disposable flush assembly 160 by extending the distal end 175 of the Y-connector luer fitting 180 within the bore 130 of the handle 126. A liquid tight seal is formed between the handle 126 and the flush assembly 160 due to the adjoining of tapered outer surface 182 of luer fitting 180 against inner wall 183 of handle 126.

Alternatively, the connector 170 on the optics harness assembly 181 and handle 126 can cooperate to directly mount the harness 181 with the handle 126 such that the fiber-optic assembly 132 extends through the bore 130 and lumen 122. The fiber-optic assembly 132 has a predetermined length such that the assembly will terminate spaced from the opening 148 when the harness assembly 181 is connected to the handle 126.

As indicated previously, the handle 126 and the Y-connector 168 are in fluid communication such that liquid flowing into the handle bore 130 from the Y-connector bore 169 will pass through the lumen 122 within shaft 112 and exit from tip 128. In addition, adjoining both the probe 162 and flush assembly 160 to the endoscope connector 170 results in the fiber-optic assembly 132 extending within the lumen of inner tube 120 and terminating within the lumen 122.

The operation of the surgical instrument depicted in FIG. 8 is similar to that of FIG. 1. However, after performing a surgical procedure, the probe assembly 162 and flush assembly 160 can be manually removed and discarded by pulling them apart from each other.

As indicated previously, the present invention also allows the disposable probe assembly 162 to be connected directly to the endoscope connector 170. As such, no flush tube assembly 160 is provided.

The probe assembly 162 is detachably coupled to connector 170 by inserting optical assembly 132 and luer fitting 173 within the opening 178 of the probe handle 126. As luer fitting 173 extends into the handle bore 130, the outer surface 173 of the luer fitting will frictionally engage against the inner wall 183 of the handle.

In the above embodiment, adjustments must be made to ensure that the terminal end of the fiber-optic assembly 132 does not extend from the tip of the probe 162. Such adjustments may include providing either an optic assembly 132 with a shorter length or a disposable probe assembly 162 having a longer shaft length.

Figure 12:
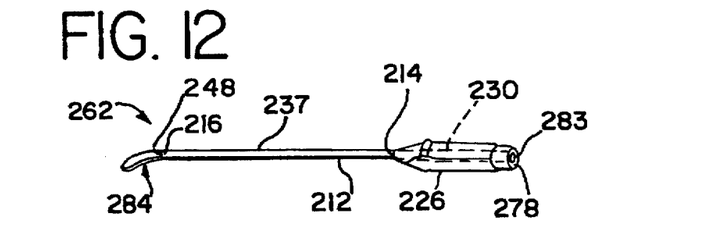
FIG. 12 is a perspective view of an alternative probe design similar to that of FIG. 11.
Figure 13:
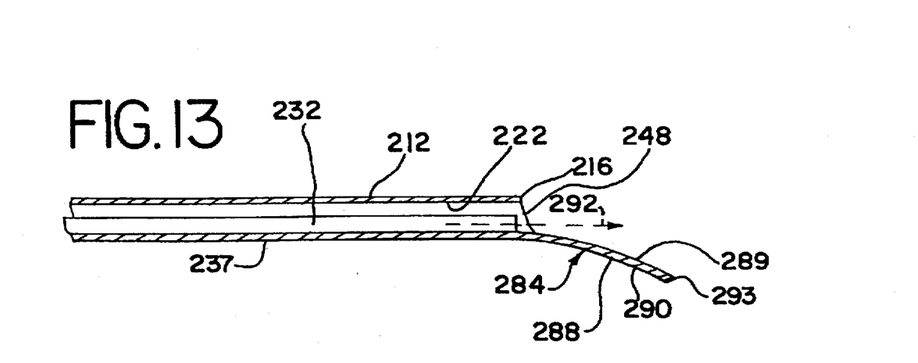
FIG. 13 is a greatly enlarged cross-sectional view of the atraumatic tip portion of the disposable probe assembly of FIG. 12 with a fiber-optic assembly disposed within the probe assembly.
Figures 14, 15, 16:
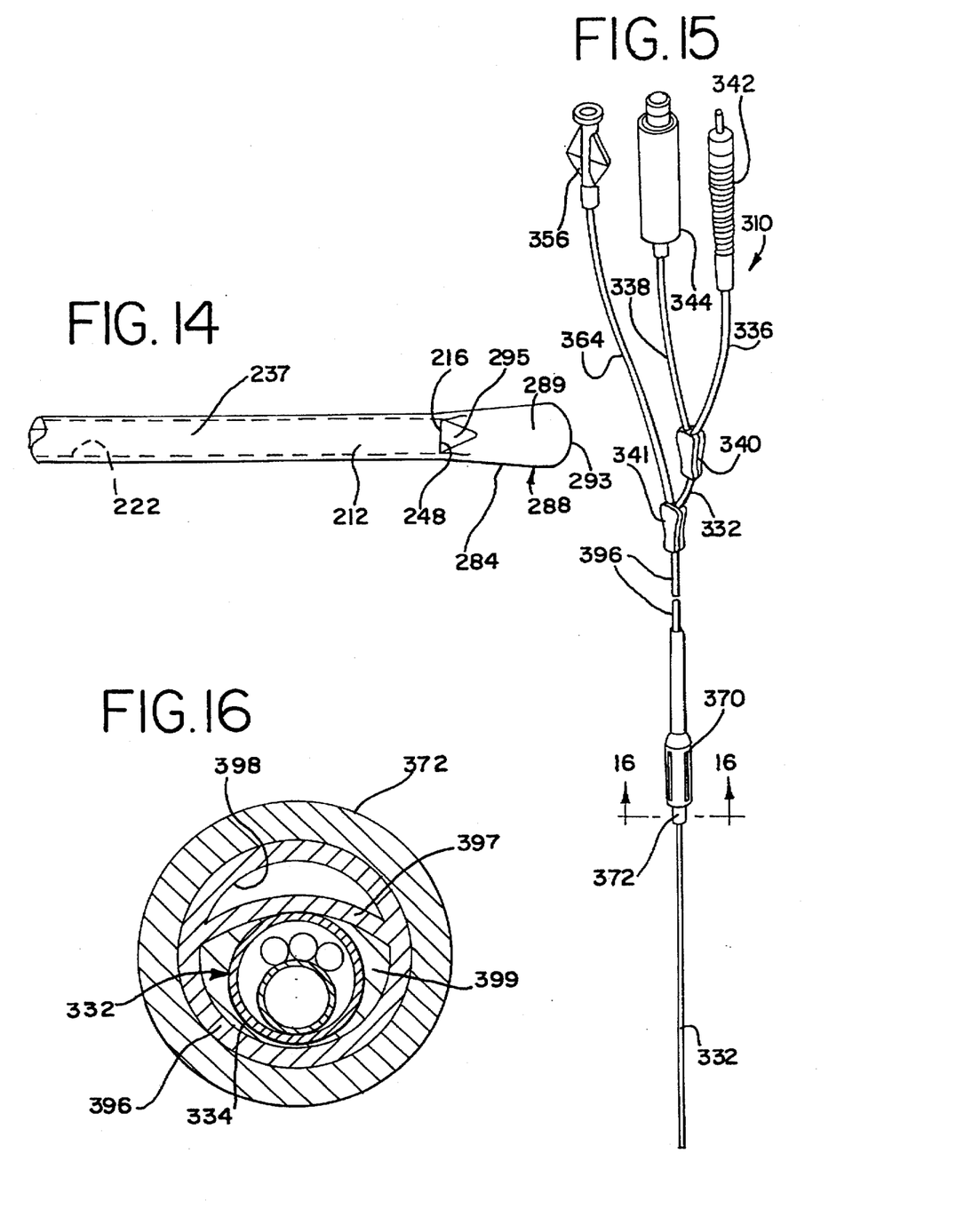
FIG. 14 is a greatly enlarged side elevation view of the tip of the probe assembly of FIG. 12 with a fiber-optic assembly extending within the assembly.
FIG. 15 is a side elevation view of another embodiment of a surgical instrument with the disposable probe assembly removed.
FIG. 16 is a greatly enlarged cross-sectional view taken along the plane 16—16 in FIG. 15.

FIGS. 12–14 provide an alternative embodiment of a disposable probe assembly 262 wherein an elevator tip 284 extends from the distal end 216 of the shaft 212. As can be seen from FIGS. 13 and 14 that shaft 212 preferably consists of a single tube 237 defining lumen 222 and extending from proximal end 214 to distal end 216. The tube 237 may consists of stainless steel and, if desired, be malleable by the surgeon such that the tube can be bent while still providing adequate tactile response or force in use. With such an embodiment, it is preferred that the harness assembly be connected directly to the handle 226 so that the fiber-optic assembly 232 is free to move slightly within the lumen 222 as the surgeon bends the tube to the desired angle or shape. This avoids placing stress on the optic fibers to prevent breakage.

It is desired that the tube 237 have a uniform outer circumference from the proximal end 214 to the distal end 216 with the proximal end 214 affixed to handle 226. Further, it is preferred that the tube 237 provides a straight length from end 214 to end 216.

Integrally formed on the distal end 216 of the shaft 212 is the rigid elevator tip 284. The tip 284 preferably provides a blade 288 for displacing tissue structures in order to gain access to a selected area to be visually observed or flushed with irrigation fluid.

The blade 288 is preferably generally spoon or dovetailed in shape with opposing bottom surface 289 and top surface 290 areas. The blade 288 extends from the shaft 212 such that the surface areas 289 and 290 outwardly expand and arch away from fiber-optic assembly line of sight 292. The terminal end 293 of the blade 288 is curved to prevent the blade 288 from easily cutting or damaging tissue. Further, to increase the amount of tissue that can be moved with the blade 288, it is desired that the surface areas 289, 290 of the blade expand to a width which is greater than the outer diameter of the shaft 212.

Preferably, the blade 288 integrally extends from the shaft 212 such that the distal end 216 of the tube 237 provides a tapered surface opening 248 to the lumen 222. Within the bottom surface area 289 is a generally semicircular indentation 295 which is concave and extends from the lumen 222 of the shaft 212. The indentation 295 provides for a gradual transition from the cylindrically shaped lumen 222 within the shaft 212 to the relatively planar bottom surface area 289 of the blade 288.

When the probe assembly 262 is detachably coupled to the flush assembly, the fiber-optic assembly 232 extends through the bore 230 of the handle 226 and into the lumen 222 of shaft 212. Preferably, the fiber-optic assembly 232 terminates within the lumen 222 and juxtapose to the surface opening 246 of the elevator tip 284. This allows the examined tissue to be brought into proper focus and prevent the fiber-optic assembly from coming into contact with the tissue.

As indicated previously, the annular space 223 formed in the lumen 222 between the tube 237 and the fiber-optic assembly 232 allows for irrigation fluid to pass through the shaft 212 and exit via the surface opening 248. The fluid can be used to clean the fiber-optic assembly 232 or the tissue area to be viewed.

During use, the surgical instrument is inserted through an opening in the body of a patient. Then, by manipulating the handle 226, the top 290 surface of the blade 288 is pressed against tissue that obstructs the area to be examined. The blade 288 elevates, or expels, the tissue and allows unobstructed access to the desired examination area.

In yet another embodiment, illustrated by FIGS. 15 and 16, the endoscope connector 70 may additionally provide for the exit of irrigation fluid from the luer fitting 72. In the embodiment, the fiber-optic assembly 332 and the hose 364 are fused together by hub 341 into a single conduit 396 which is preferably made of flexible plastic. The conduit 396 provides a partition 397 which separates passage 398 from the fiber-optic assembly 332. The passage 398 extends within the conduit 396 and is in fluid communication with hose 364. This allows an irrigation solution to be injected into connector 356, pass through the connector 370, and exit from the distal end of luer fitting 372.

Referring particularly to FIG. 16, the fiber-optic assembly 332 is secured within the conduit 396 by an adhesive 399 such as epoxy. Further, the adhesive 399 prevents irrigation fluid from re-entering the conduit 396 once the fluid exits from passage 398.

The endoscope connector 370 provides luer fitting 372 for detachably securing a probe assembly to the connector. Once secured, the fiber-optic assembly 332 extends within the lumen of the probe assembly shaft. Further, the lumen of the probe assembly and connector passage 398 are in fluid communication with each other such that fluid provided at connector 356 will exit from the surface opening of the probe assembly.

Figure 17:
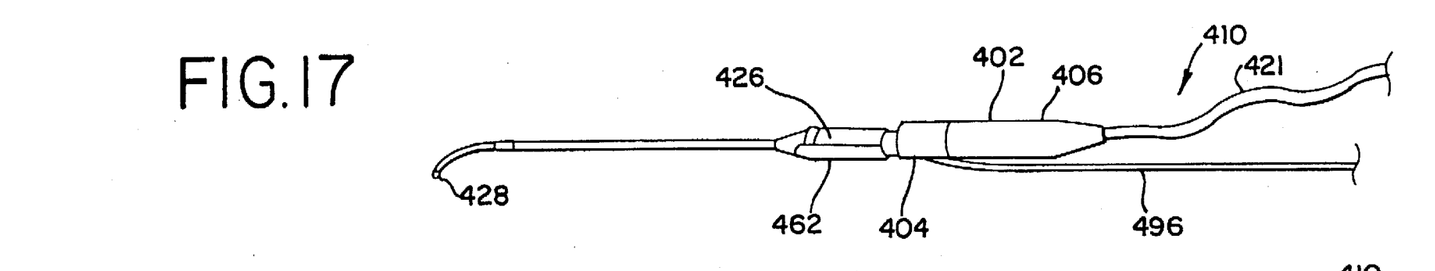
FIG. 17 is a side elevation view of yet another embodiment of a surgical instrument.
Figure 18:
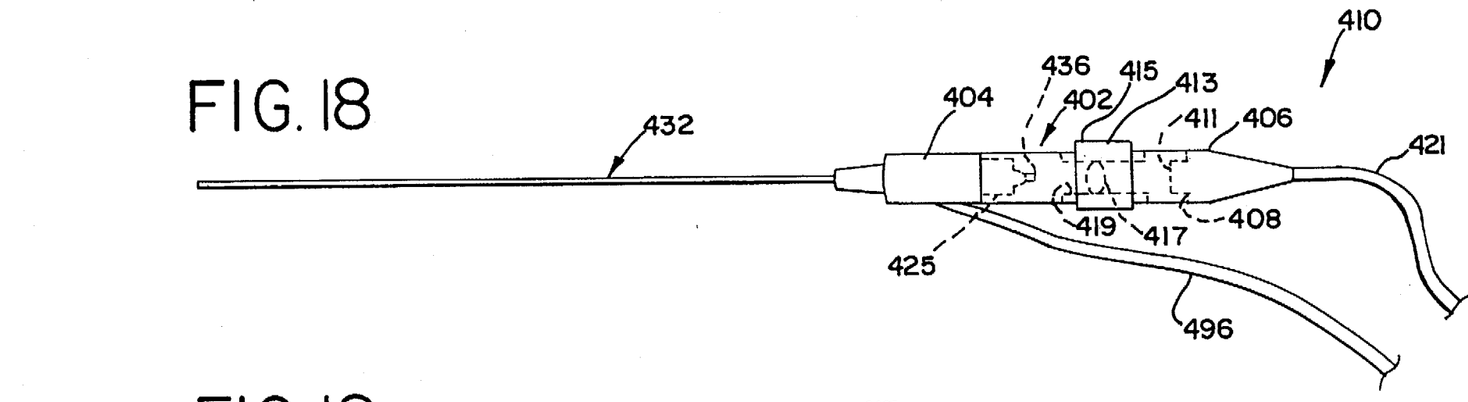
FIG. 18 is a side elevation view of a fiber-optic assembly and a CCD camera head assembly in accordance with an embodiment of the invention similar to the embodiment of FIG. 17 with the probe assembly removed.
Figure 19:
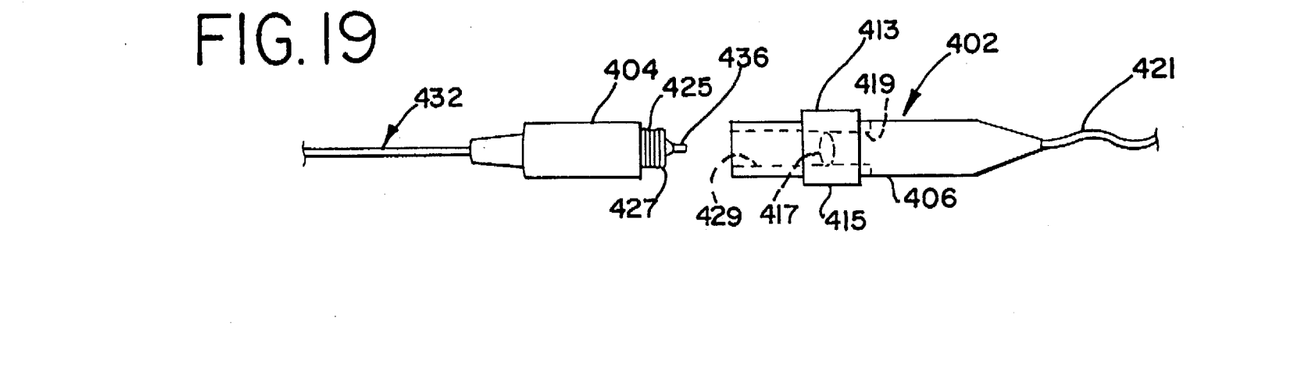
FIG. 19 is a broken view illustrating the fiber-optic assembly, the camera head assembly and means for securing together the fiber-optic assembly and the CCD camera head assembly in accordance with the embodiment of FIG. 18.

FIGS. 17–19 illustrate a surgical instrument 410 in accordance with another alternative embodiment of the invention. In the embodiment depicted in FIGS. 17–19, the probe assembly 462 is secured to a camera such as a Charged-Coupled Device (CCD) camera head assembly 402 by, for example, a second connector 404 extending from the fiber-optic assembly 432.

The CCD camera head assembly 402 includes a casing 406, a CCD camera head 408, a CCD chip 411, and a focusing lens system 413 for focusing an image onto the CCD chip 411. The CCD camera head 408 preferably has an outer diameter of about ¼ inch (about 7 mm). In the embodiment of FIGS. 18 and 19, the focusing lens system 413 includes a focusing ring 415 and a lens 417, and a channel 419 is defined within the casing 406 to permit sliding of the lens 417 by the focusing ring 415 to bring the image into focus. An electric cord 421 extends from the CCD camera head assembly 402 to a television monitor. A conduit 496 extends from the second connector 404 that contains illumination fibers and, if desired, an irrigation tube.

A proximal end of the second connector 404 is removably secured to the CCD camera head assembly 402 preferably so that a distal end of an image fiber bundle 436 extending from the fiber-optic assembly 432 is a predetermined distance from the CCD camera head 408 or the focusing lens 417 so that the image can readily be brought into focus. In the illustrative embodiment, a first mating portion 425 having a male thread 427 is defined at the proximal end of the second connector 404. A second mating portion 429 having a female thread is defined at a distal end of the casing 406 of the CCD camera head assembly 402. The first mating portion 425 is adapted to extend within the casing 406 and threadingly engage the second mating portion 429.

The embodiment of FIGS. 17–19 provides many advantages. For example, it enables the fiber-optic assembly to be readily and easily secured adjacent the CCD camera head 408 so that the distal end of the image fiber bundle 436 and the focusing lens 417 or CCD camera head are spaced apart by a predetermined distance. Thus, the image can be readily and easily brought into focus. With this construction, the fiber-optic assembly 432 can be disposable, with the camera head assembly 402 being reusable with other fiber-optic assemblies. This is a significant advantage because CCD chips and camera heads tend to be relatively expensive components.

With the embodiments of FIGS. 17–19, the CCD camera head 408 is positioned at a location that does not interfere with the surgical procedure and does not significantly affect the control and tactile feel of the instrument. The CCD camera head is sufficiently close to the surgical site, yet positioned so that it should not come into contact with the surgical site. The camera head assembly 402 also preferably is compact and lightweight so that it does not add any significant bulk or weight to the surgical instrument. These embodiments also permit the CCD camera head to be heavily insulated by the casing 406 or other suitable insulation without interfering with the surgical procedure and without significantly affecting the control and tactile feel of the instrument.

What is claimed is:

1. A surgical instrument for examining tissue comprising:
   (a) an elongated substantially rigid shaft having a proximal end, a distal end and a lumen extending between the ends;
   (b) a handle connected to the proximal end of the shaft, the handle including a longitudinal bore communicating with the lumen;
   (c) an expanded rigid atraumatic tip on the distal end of the shaft, the tip defining a surface opening that communicates with the lumen; and
   (d) a fiber-optic viewing assembly including a plurality of optical image fibers and having an objective lens mounted within the lumen for creating an optical image of tissue proximal to the opening, the assembly being mounted to extend and terminate within the lumen such that the tissue can be examined.

2. The surgical instrument of claim 1 wherein the expanded tip forms an elevator.

3. The surgical instrument of claim 1 wherein the expanded tip is a blade that arches from the shaft.

4. The surgical instrument of claim 3 wherein the blade has an arcuate distal end.

5. The surgical instrument of claim 1 wherein the expanded tip is bulbous.

6. The surgical instrument of claim 5 wherein the expanded tip and the shaft are formed from a single tube.

7. The surgical instrument of claim 5 wherein the proximal end of the shaft has an outer diameter and the expanded tip has an outer diameter which is less than the outer diameter of the shaft.

8. The surgical instrument of claim 1 wherein the handle is detachably coupled to an endoscope connector, the connector including a passage in fluid communication with the bore of the handle.

9. The surgical instrument of claim 1 wherein the handle is detachably coupled to a Y-connector forming a passage, the Y-connector attached to a hose including a lumen, the passage and lumen in fluid communication with the bore of the handle.

10. The surgical instrument of claim 1 wherein the lumen and fiber-optic assembly define a space between them that is in fluid communication with the opening to allow a flushing fluid to be sent through the lumen and out the opening.

11. The surgical instrument of claim 10 wherein the fluid enters the lumen about the objective lens.

12. The surgical instrument of claim 1 wherein the fiber-optic viewing assembly extends from an endoscope connector, the endoscope connector being detachably connected to the handle.

13. The surgical probe of claim 1 wherein the tip is generally spherical and symmetrically joined on the shaft and has a diameter about twice that of the shaft to permit tissue to close about the shaft and open in front of the opening.

14. The surgical instrument of claim 1 wherein the objective lens is recessed a predetermined distance from the opening such that tissue at the opening is in focus.

15. The surgical instrument of claim 1 wherein the shaft includes an arcuate bend proximal of the atraumatic tip.

16. The surgical instrument of claim 1 wherein the axis of the fiber-optic assembly is eccentric to the axis of the lumen.

17. The surgical instrument of claim 1 further including at least one illumination fiber extending through the longitudinal bore and the lumen for transmitting light energy from an external source proximal of the handle and through the opening.

18. The surgical instrument of claim 1 wherein the fiber-optic assembly is removably mounted on the handle.

19. The surgical instrument of claim 18 including the cooperating connectors on the fiber-optic assembly and handle and wherein a distal portion of fiber optic assembly has a predetermined length to extend through the bore and lumen with the fiber-optic assembly terminating within the lumen spaced from the opening.

20. The surgical instrument of claim 1 including a camera mounted on the handle operably associated with the fiber-optic assembly.

21. The surgical instrument of claim 1 wherein the opening in the tip is generally coaxial with the lumen.

22. The surgical instrument of claim 1 wherein the opening is located at an angle to a longitudinal axis of the lumen.

23. The surgical instrument of claim 1 wherein at least a portion of the shaft is malleable by a user.

24. A surgical instrument comprising:
   (a) an elongated rigid shaft having a proximal end, a distal end and a lumen extending between the ends;
   (b) a handle affixed to the proximal end of the shaft, the handle including a longitudinal bore communicating with the lumen;
   (c) a rigid expanded tip on the distal end of the shaft and projecting from the diameter of the shaft, the tip defining an opening communicating with the lumen;
   (d) an optic harness assembly removably mounted on the handle with a fiber-optic assembly extending into the lumen for creating, at a remote location, a viewable image of tissue located proximal and exterior to the tip; and
   (e) an endoscope connector attached to the fiber-optic viewing assembly and detachably coupled to the handle, the fiber-optic viewing assembly extending a predetermined length from the endoscope connector such that the fiber-optic assembly terminates within the lumen.

25. The surgical instrument of claim 24 wherein the expanded tip is joined to the distal end of the shaft and forms an elevator.

26. The surgical instrument of claim 24 wherein the expanded tip has a generally dovetailed shape and is joined to the distal end of the shaft, the tip arcing from the shaft and having a tapered terminal end.

27. The surgical instrument of claim 24 wherein the endoscope connector includes a longitudinal port in fluid communication with the bore of the handle.

28. The surgical instrument of claim 24 wherein the fiber-optic assembly has a proximal end and a distal end and including at least one illumination fiber, a plurality of image fibers and an objective lens affixed to the distal end, the objective lens mounted in the tip to receive light traversing the illumination fiber and reflected from an object being viewed.

29. The surgical instrument of claim 28 further including flushing means for injecting a flushing liquid through the lumen for maintaining the objective lens clean of blood and debris.

30. The surgical instrument of claim 25 wherein the shaft is malleable by a user.

31. The surgical instrument of claim 25 wherein an annular space is defined between the shaft, the tip and the fiber-optic assembly within the lumen and bore to provide flushing liquid to the tip.

32. The surgical instrument of claim 25 wherein the shaft includes a flush lumen therein parallel to the fiber-optic assembly to provide liquid to the opening.

33. A surgical instrument for elevating and viewing tissue comprising:
 (a) an elongated rigid shaft having a proximal end, a distal end and a lumen extending between the ends;
 (b) a handle connected to the proximal end of the shaft, the handle including a longitudinal bore communicating with the lumen;
 (c) a rigid spread atraumatic tip associated with the distal end of the shaft, the tip defining an opening that communicates with the lumen; and
 (d) a fiber-optic viewing assembly including a plurality of optical image fibers having a planar face at the distal end thereof, the assembly extending through the shaft and including an objective lens for creating an optical image of tissue proximal to the opening onto the fact of the image fibers, the assembly terminating within the lumen such that the tissue can be positioned and viewed simultaneously,
 the lumen being in fluid communication with the opening to allow a fluid to be sent through the lumen, about the objective lens and out the opening.

34. The surgical instrument of claim 33 wherein the fiber-optic viewing assembly is disposed in the lumen.

35. The surgical instrument of claim 33 further including an endoscope connector attached to the fiber-optic viewing assembly and detachably coupled to the handle.

\* \* \* \* \*